United States Patent
Zoller et al.

[11] Patent Number: 5,939,556
[45] Date of Patent: Aug. 17, 1999

[54] HYDANTOIN COMPOUNDS, SALTS THEREOF, PROCESSES FOR THEIR PREPARATION, AND PROCESSES FOR PREPARING PHARMACEUTICALLY ACTIVE COMPOUNDS COMPRISING THEM

[75] Inventors: Gerhard Zoller, Schöneck; Otmar Klingler, Rodgau; Jochen Knolle, Kriftel; Hans Ulrich Stilz, Frankfurt; Volkmar Wehner, Sandberg, all of Germany

[73] Assignee: Hoechst Aktiengesellschaft, Frankfurt am Main, Germany

[21] Appl. No.: 08/952,322

[22] PCT Filed: Apr. 15, 1996

[86] PCT No.: PCT/EP96/01572

§ 371 Date: Oct. 27, 1997

§ 102(e) Date: Oct. 27, 1997

[87] PCT Pub. No.: WO96/33976

PCT Pub. Date: Oct. 31, 1996

[30] Foreign Application Priority Data

Apr. 28, 1995 [DE] Germany ............ 195 15 177

[51] Int. Cl.$^6$ ............ C07D 233/76; C07D 233/74; C07D 233/72; A61K 31/415
[52] U.S. Cl. ............ 548/320.1; 514/398; 548/315.1; 548/317.1; 548/321.1; 548/324.1; 548/325.1
[58] Field of Search ............ 548/320.1, 315.1; 514/398

[56] References Cited

U.S. PATENT DOCUMENTS

| | | | |
|---|---|---|---|
| 2,972,618 | 2/1961 | Bortnick ............ | 548/320.1 X |
| 3,818,032 | 6/1974 | Moser et al. ............ | 548/320.1 X |
| 4,428,948 | 1/1984 | Miller et al. ............ | 424/244 |
| 5,389,614 | 2/1995 | König et al. ............ | 514/18 |
| 5,608,076 | 3/1997 | Kottenhahn et al. ............ | 548/317.1 |

FOREIGN PATENT DOCUMENTS

| | | | |
|---|---|---|---|
| 0578516 | 1/1994 | European Pat. Off. ............ | 548/321.1 |
| 4338944 | 5/1995 | Germany . | |
| 4427979 | 2/1996 | Germany . | |
| 62-175470 | 8/1987 | Japan ............ | 548/320.1 |
| 95/14008 | 5/1995 | WIPO . | |

OTHER PUBLICATIONS

Connors et al., J. Chem. Soc., "Aryl–2–halogenalkylamines. Part XIX. Some NN–Di–chloroethyl–aminophenyl— and –phenylalkylhydantoins and Related Amino–acids," pp. 2994–3007 (1960).
Derwent Abstract of DE–A–4338944.
Derwent Abstract of DE–A–4427979.

*Primary Examiner*—Floyd D. Higel
*Attorney, Agent, or Firm*—Finnegan, Henderson, Farabow, Garrett & Dunner, L.L.P.

[57] ABSTRACT

The present invention relates to hydantoin derivatives of the formula I

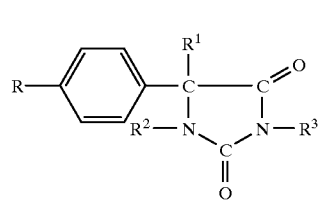

and which are intermediates for the preparation of pharmaceutical active compounds, their preparation and their use in the preparation of the active compounds.

22 Claims, No Drawings

HYDANTOIN COMPOUNDS, SALTS THEREOF, PROCESSES FOR THEIR PREPARATION, AND PROCESSES FOR PREPARING PHARMACEUTICALLY ACTIVE COMPOUNDS COMPRISING THEM

This application is a 35 U.S.C. § 371 national application of international application PCT/EP96/01572, filed Apr. 15, 1996.

The present invention relates to hydantoin derivatives of the formula I

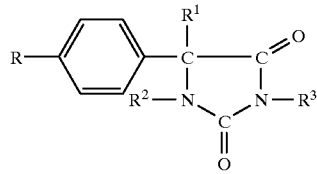

which are valuable intermediates for the preparation of pharmaceutical active compounds, their preparation and their use in the preparation of the active compounds.

In German Patent Applications P 43 38 944 and P 44 27 979 and the PCT Application PCT/EP94/03491, substituted 5-membered ring heterocycles are described which inhibit cell-cell adhesion, in particular, for example, platelet aggregation. These active compounds contain a polysubstituted imidazolidine, oxazolidine, thiazolidine or pyrrolidine ring which is linked to an unsubstituted or substituted amino, amidino or guanidino group yla a bivalent group, e.g. yla an alkylene group or yla various other groups. The heterocyclic 5-membered ring has an asymmetric center. In particular for a group of these active compounds which contain a 2,5-dioxoimidazolidine ring, i.e. a hydantoin ring, which is linked yla a 1,4-phenylene unit to the amino or aminomethyl, amidino or guanidino group, it has proven advantageous, especially in the preparation of active compounds haylng a uniform configuration at the asymmetric center of the 5-membered ring, to start from the corresponding hydantoins of the formula I as intermediates.

The present invention therefore relates to hydantoin derivatives of the formula I

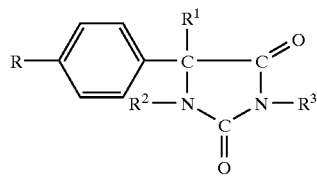

in which

R is cyano, $C(=NH)-O-(C_1-C_6)$-alkyl, $C(=NH)-NH-X$, $CH_2-NH-X$ or $NH-X^1$;

X is hydrogen, $(C_1-C_6)$-alkyl, $(C_1-C_6)$-alkylcarbonyl, $(C_1-C_6)$-alkoxycarbonyl, $(C_1-C_{18})$-alkylcarbonyloxy-$(C_1-C_6)$-alkoxycarbonyl, optionally substituted $(C_6-C_{14})$-arylcarbonyl, optionally substituted $(C_6-C_{14})$-aryloxycarbonyl, $(C_6-C_{14})$-aryl-$(C_1-C_6)$-alkoxycarbonyl which can also be substituted in the aryl radical, $(R^5O)_2P(O)$, cyano, hydroxyl, $(C_1-C_6)$-alkoxy, $(C_6-C_{14})$-aryl-$(C_1-C_6)$-alkoxy which can also be substituted in the aryl radical, or amino;

$X^1$ has one of the meanings of X or is R'—NH—C(=N—R"), where R' and R" independently of one another have the meanings of X;

$R^1$ is $(C_1-C_8)$-alkyl, $(C_6-C_{14})$-aryl-$(C_1-C_8)$-alkyl optionally substituted in the aryl radical or $(C_3-C_8)$-cycloalkyl;

$R^2$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical or $(C_3-C_8)$-cycloalkyl;

$R^3$ is hydrogen or $CH_2$—CO—$OR^4$;

$R^4$ is hydrogen, $(C_1-C_6)$-alkyl, $(C_6-C_{14})$-aryl-$(C_1-C_6)$-alkyl optionally substituted in the aryl radical or optionally substituted $(C_6-C_{14})$-aryl;

$R^5$ is hydrogen, $(C_1-C_8)$-alkyl, optionally substituted $(C_6-C_{14})$-aryl or $(C_6-C_{14})$-aryl-$(C_1-C_8)$-alkyl, which can also be substituted in the aryl radical;

where, however, if $R^3$ is hydrogen, R cannot be CN, $NH_2$ or $CH_2$—$NH_2$;

and where, if the compounds of the formula I are present in racemic form with respect to the asymmetric center in the hydantoin ring and at the same time $R^3$ is methoxycarbonylmethyl, $R^1$ is methyl and $R^2$ is hydrogen or methyl, R cannot be CN or C(=NH)—$OC_2H_5$;

and where, if the compounds of the formula I are present in racemic form with respect to the asymmetric center in the hydantoin ring and at the same time $R^3$ is methoxycarbonylmethyl or hydroxycarbonylmethyl, $R^1$ is methyl and $R^2$ is hydrogen or methyl, R cannot be $NH_2$, $CH_2$—$NH_2$, $C(=NH)$—$NH_2$, tert-butoxycarbonyl-aminomethyl or benzyloxycarbonylguanidino; and their salts.

The present invention relates to all stereoisomeric forms of the compounds of the formula I. There are thus included, in particular if beside the asymmetric center in the hydantoin ring no other optically active centers are present, the enantiomers with R configuration and those with S configuration on the hydantoin carbon atom and, beside the pure enantiomers, also the racemate and mixtures of the enantiomers in any desired quantitative ratios. If, beside the optically active carbon atom in the hydantoin ring, other asymmetric centers are present, e.g. in alkyl, cycloalkyl or arylalkyl radicals, the optically active atoms in the molecule can independently of one another have the R or S configuration, and in each of these centers, independently of the others, a uniform configuration can be present or a mixture of the configuration-isomeric forms in the ratio 1:1 or in any desired quantitative ratio can be present. The present invention thus includes both all pure enantiomers and enantiomer mixtures and all diastereomers and diastereomer mixtures. It also includes salts of the compounds of the formula I with optically active acids or bases.

The compounds of the formula I can contain mobile hydrogen atoms, i.e. be present in various tautomeric forms. The present invention also relates to all these tautomers.

Cycloalkyl radicals are, in particular, cyclopropyl, cyclobutyl, cyclopentyl, cyclohexyl, cycloheptyl and cyclooctyl, which, however, can also be substituted by, for example, $(C_1-C_4)$-alkyl. Examples of substituted cycloalkyl radicals are 4-methylcyclohexyl and 2,3-dimethylcyclopentyl.

Alkyl radicals can be straight-chain or branched. This also applies if they carry substituents or occur as substituents of other radicals, for example in alkylcarbonyl, alkoxy, alkoxycarbonyl or aralkyl radicals.

Examples of suitable $C_1-C_{18}$-alkyl radicals are: methyl, ethyl, propyl, butyl, pentyl, hexyl, heptyl, octyl, decyl, undecyl, dodecyl, tridecyl, pentadecyl, hexadecyl, heptadecyl, octadecyl, isopropyl, isobutyl, isopentyl, neopentyl, isohexyl, 3-methylpentyl, 2,3,5-trimethylhexyl, sec-butyl, tert-butyl, tert-pentyl. Preferred alkyl radicals are methyl, ethyl, propyl, isopropyl, butyl, isobutyl, sec-butyl and tert-butyl.

($C_6$–$C_{14}$)-Aryl groups are, for example, phenyl, naphthyl, biphenylyl or fluorenyl, 1-naphthyl, 2-naphthyl and, in particular, phenyl being preferred. Aryl radicals, in particular phenyl radicals, can be unsubstituted or mono- or polysubstituted, preferably mono-, di- or trisubstituted, by identical or different radicals, in particular by radicals from the group consisting of ($C_1$–$C_8$)-alkyl, in particular ($C_1$–$C_4$)-alkyl, ($C_1$–$C_8$)-alkoxy, in particular ($C_1$–$C_4$)-alkoxy, halogen, nitro, amino, trifluoromethyl, hydroxyl, methylenedioxy, cyano, hydroxycarbonyl, aminocarbonyl, ($C_1$–$C_4$)-alkoxycarbonyl, phenyl, phenoxy, benzyloxy, ($R^5O)_2P(O)$, ($R^5O)_2P(O)$—O—, tetrazolyl. The same applies, for example, to radicals such as aralkyl or arylcarbonyl. Aralkyl radicals are, in particular, benzyl as well as 1- and 2-naphthylmethyl and 9-fluorenylmethyl, which can also be substituted. Substituted aralkyl radicals are, for example, halobenzyl or ($C_1$–$C_4$)-alkoxybenzyl.

In monosubstituted phenyl radicals, the substituent can be in the 2-, the 3- or the 4-position, the 3- and the 4-position being preferred. If phenyl is disubstituted, the substituents can be in the 1,2-, 1,3- or 1,4-position relative to one another. Preferably, in disubstituted phenyl radicals the two substituents are arranged in the 3- and the 4- or the 3- and the 5-position, relative to the linkage site.

Halogen is fluorine, chlorine, bromine or iodine, in particular fluorine or chlorine.

Functional groups in the compounds of the formula I can be present in protected form. Suitable protective groups such as, for example, urethane protective groups or carboxyl protective groups are described in Hubbuch, Kontakte (Merck) 1979, No. 3, pages 14 to 23 and in Bullesbach, Kontakte (Merck) 1980, No. 1, pages 23 to 35. The following may be mentioned in particular: Aloc, Pyoc, Fmoc, Tcboc, Z, Boc, Ddz, Bpoc, Adoc, Msc, Moc, Z($NO_2$), Z($Hal_n$), Bobz, Iboc, Adpoc, Mboc, Acm, tert-butyl, OBzl, ONbzl, OMbzl, Bzl, Mob, Pic, Trt.

Salts of the compounds of the formula I can have advantages in the preparation or isolation of the compounds of the formula I, their storage or subsequent reaction. In the case of compounds of the formula I which contain acidic groups, e.g. carboxyl, such salts can be, for example, alkali metal or alkaline earth metal salts, such as, for example, lithium, sodium, potassium, magnesium or calcium salts, as well as salts with ammonia or organic amines, such as, for example, triethylamine, ethyidiisopropylamine, n-ethylmorpholine, pyridine or optically active bases such as, for example, 1-phenylethylamine.

Compounds of the formula I which contain basic groups, e.g. an amino group, an amidino group or a guanidino group, can form salts with inorganic acids, such as, for example, hydrochloric acid, hydrobromic acid, hydriodic acid, tetrafluoroboric acid, sulfuric acid or phosphoric acid, and with organic carboxylic or sulfonic acids, such as, for example, acetic acid, citric acid, benzoic acid, maleic acid, fumaric acid, tartaric acid and other optically active acids, methanesulfonic acid, naphthalenesulfonic acids or p-toluenesulfonic acid.

R is preferably cyano or C(=NH)—NH—X.

X is preferably hydrogen, ($C_1$–$C_6$)-alkylcarbonyl, ($C_1$–$C_6$)-alkoxycarbonyl or ($C_6$–$C_{14}$)-aryl-($C_1$–$C_6$)-alkoxycarbonyl optionally substituted in the aryl radical, particularly preferably hydrogen.

$R^1$ is preferably ($C_1$–$C_8$)-alkyl, phenyl-($C_1$–$C_8$)-alkyl optionally substituted in the phenyl radical or ($C_3$–$C_8$)-cycloalkyl, particularly preferably ($C_1$–$C_4$)-alkyl, cyclopropyl or benzyl, very particularly preferably methyl.

$R^2$ is preferably hydrogen, ($C_1$–$C_8$)-alkyl, optionally substituted phenyl, phenyl-($C_1$–$C_8$)-alkyl optionally substituted in the phenyl radical or ($C_3$–$C_8$)-cycloalkyl, particularly preferably hydrogen or ($C_1$–$C_4$)-alkyl, very particularly preferably hydrogen.

$R^3$ is preferably $CH_2$—CO—$OR^4$, particularly preferably $CH_2$—COOH.

$R^4$ is preferably hydrogen or ($C_1$–$C_4$)-alkyl.

A uniform configuration is preferably present at the asymmetric center in the hydantoin ring, particularly preferably the S configuration.

Preferred compounds of the formula I are those in which one or more substituents have preferred meanings. Particularly preferred compounds of the formula I are those in which R is cyano or C(=NH)—NH—X;

X is hydrogen, ($C_1$–$C_6$)-alkylcarbonyl, ($C_1$–$C_6$)-alkoxycarbonyl or optionally substituted ($C_6$–$C_{14}$)-aryl-($C_1$–$C_6$)-alkoxycarbonyl;

$R^1$ is ($C_1$–$C_8$)-alkyl, ($C_6$–$C_{14}$)-aryl-($C_1$–$C_8$)-alkyl optionally substituted in the aryl radical or ($C_3$–$C_8$)-cycloalkyl;

$R^2$ is hydrogen, ($C_1$–$C_8$)-alkyl, optionally substituted phenyl, phenyl-($C_1$–$C_8$)-alkyl optionally substituted in the phenyl radical or ($C_3$–$C_8$)-cycloalkyl;

$R^3$ is $CH_2$—CO—$OR^4$;

$R^4$ is hydrogen, ($C_1$–$C_6$)-alkyl, ($C_6$–$Cl_4$)-aryl-($C_1$–$C_6$)-alkyl optionally substituted in the aryl radical or optionally substituted ($C_6$–$C_{14}$)-aryl;

where, however, if the compounds of the formula I are present in racemic form with respect to the asymmetric center in the hydantoin ring and at the same time $R^3$ is methoxycarbonylmethyl, $R^1$ is methyl and $R^2$ is hydrogen or methyl, R cannot be CN;

and where, if the compounds of the formula I are present in racemic form with respect to the asymmetric center in the hydantoin ring and at the same time $R^3$ is methoxycarbonylmethyl or hydroxycarbonylmethyl, $R^1$ is methyl and $R^2$ is hydrogen or methyl, R cannot be C(=NH)—$NH_2$.

Very particularly preferred compounds of the formula I are those in which

R is cyano or C(=NH)—$NH_2$;

$R^1$ is ($C_1$–$C_4$)-alkyl, cyclopropyl or benzyl, in particular methyl;

$R^2$ is hydrogen or ($C_1$–$C_4$)-alkyl, in particular hydrogen;

$R^3$ is $CH_2$—COOH or $CH_2$—COO—($C_1$–$C_4$)-alkyl, in particular $CH_2$—COOH;

where, however, if the compounds of the formula I are present in racemic form with respect to the asymmetric center in the hydantoin ring and at the same time $R^3$ is methoxycarbonylmethyl, $R^1$ is methyl and $R^2$ is hydrogen or methyl, R cannot be CN;

and where, if the compounds of the formula I are present in racemic form with respect to the asymmetric center in the hydantoin ring and at the same time $R^3$ is methoxycarbonylmethyl or hydroxycarbonylmethyl, $R^1$ is methyl and $R^2$ is hydrogen or methyl, R cannot be C(=NH)—$NH_2$.

Moreover, preferred compounds of the formula I are those which are present in enantiomerically pure form with respect to the asymmetric center in the hydantoin ring, in particular the isomers haylng the S configuration.

Also, in all preferred compounds of the formula I, of course, the salts are likewise a subject of the present invention.

The compounds of the formula I according to the invention can be prepared by various routes, for example the routes A, B and C explained below, it frequently being possible to carry out the individual steps according to or analogously to procedures known from the literature.

Route A:

Compounds of the formula I can be prepared by reacting compounds of the formula II

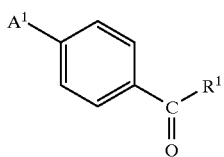
(II)

in which $A^1$ is halogen, preferably bromine, or nitro and $R^1$ has the meanings indicated above, under the known conditions of the Bucherer reaction to give compounds of the formula III

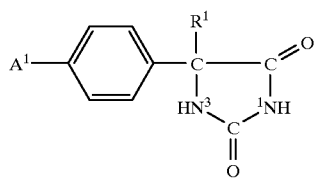
(III)

from which by hydrolysis of the hydantoin, e.g. with sodium hydroxide solution, following the process described by H. T. Bucherer and V. A. Lieb, J. Prakt, Chem. 141 (1934), 5, the amino acids of the formula IV

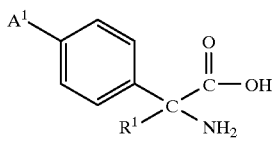
(IV)

can be obtained. From these, according to known methods (see, for example, L. Birkhofer and R. Modic, Liebigs Ann. Chem. 628 (1959), 168) the amino acid esters of the formula V

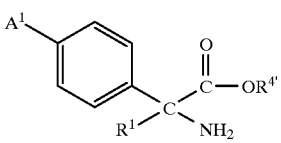
(V)

are obtainable, in which $R^{4'}$ can have the meanings indicated above for $R^4$ with the exception of hydrogen. These can be reacted with isocyanatoacetic acid esters of the formula VI

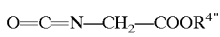
$$O=C=N-CH_2-COOR^{4''} \qquad (VI)$$

in which $R^{4''}$ likewise can have the meanings indicated above for $R^4$ with the exception of hydrogen, to give the compounds of the formula VII

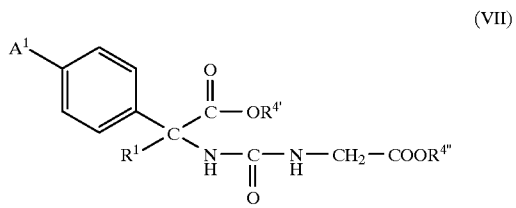
(VII)

which can be cyclized under acidic conditions, e.g. in aqueous acid, to give the hydantoin acetic acids of the formula VIII

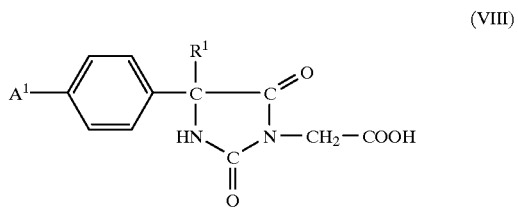
(VIII)

Compounds of the formula VIII in which $A^1$ is halogen can be converted by methods known per se (see, for example, G. P. Ellis and T. M. Romney-Alexander, Chem. Rev. 87 (1987), 779–794), e.g. by a bromine-cyano replacement, into compounds of the formula Ia

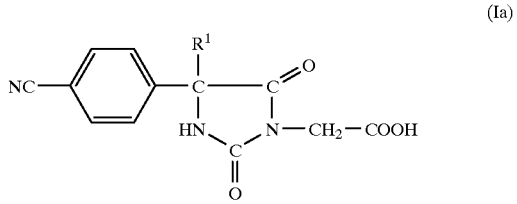
(Ia)

compounds of the formula I in which R has the meaning $C(=NH)-O-(C_1-C_6)$-alkyl are obtainable from the compounds of the formula Ia by addition of the $(C_1-C_6)$-alkanols in acidic anhydrous medium, e.g. in dioxane or in anhydrous pure alcohol. Subsequent aminolysis of the imido acid esters, e.g. by treatment with ammonia in alcohols, such as methanol, ethanol or isopropanol (see, for example, G. Wagner, P. Richter and C. Grabe, Pharmazie 29 (1974), 12–15), leads to amidines, i.e. compounds of the formula I in which R has the meaning $C(=NH)NH_2$. Another method of preparing amidines is the addition of hydrogen sulfide to the cyano group of the compounds of the formula Ia, followed by methylation of the resulting thioamide and subsequent reaction, for example with ammonia (cf. GDR Patent No. 235 866). Compounds of the formula I in which R has the meaning $CH_2NH_2$ can be prepared from the compounds of the formula Ia by reduction of the cyano group by methods known per se.

Compounds of the formula VIII in which $A^1$ is $NO_2$ can be converted according to methods known per se by reduction of the nitro group into compounds of the formula I in which R has the meaning $NH_2$. A guanidino group can be obtained from this amino function using the following reagents:

1. O-Methylisourea (S. Weiss and H. Krommer, Chemiker-Zeitung 98 (1974), 617–618),
2. S-Methylisothiourea (R. F. Borne, M. L. Forrester and I. W. Waters, J. Med. Chem. 20 (1977), 771–776),
3. Nitro-S-methylisothiourea (L. S. Hafner and R. Evans, J. Org. Chem. 24 (1959), 1157),
4. Formamidinosulfonic acid (K. Kim, Y.-T. Lin and H. S. Mosher, Tetrahedron Lett. 29 (1988), 3183–3186),
5. 3,5-Dimethyl-1-pyrazolylformamidinium nitrate (F. L. Scott, D. G. O'Donovan and J. Reilly, J. Amer. Chem. Soc. 75 (1953), 4053–4054),
6. N, N'-Di-tert-butoxycarbonyl-S-methylisothiourea (R. J. Bergeron and J. S. McManis, J. Org. Chem. 52 (1987), 1700–1703),
7. N-Alkoxycarbonyl-, N,N'-dialkoxycarbonyl-, N-alkylcarbonyl- and N,N'-dialkylcarbonyl-S-methylisothiourea (H. Wollweber, H. Kolling, E. Niemers, A. Widding, P. Andrews, H.-P. Schulz and H. Thomas, Arzneim. Forsch./Drug Res. 34 (1984), 531–542).

Compounds of the formula I in which $R^3$ is $CH_2$—$COOR^4$ and $R^4$ has a meaning other than hydrogen can be obtained from the compounds of the formula VIII by esterification of the carboxyl group according to methods known per se and subsequent transformation of the radical $A^1$ into the radical R as described above. Compounds of the formula I in which $R^2$ has a meaning other than hydrogen are obtainable from the compounds of the formula VIII esterified on the carboxyl group by alkylation, cycloalkylation, arylation or aralkylation on the NH group of the hydantoin according to methods known per se and subsequent transformation of the radical $A^1$ into the radical R as described above. Compounds of the formula I in which $R^2$ has a meaning other than hydrogen and $R^3$ has the meaning $CH_2$—COOH are obtained from the carboxylic acid esters by repeated hydrolysis.

Compounds of the formula I in which $R^3$ has the meaning hydrogen can be obtained, if $R^2$ has the meaning hydrogen, from the compounds of the formula III by the transformations of the radical $A^1$ into the radical R described above. Compounds of the formula I in which $R^3$ has the meaning hydrogen and $R^2$ has a meaning other than hydrogen can be obtained from the compounds of the formula III by protection of the $N^1H$ function, alkylation, cycloalkylation, arylation or aralkylation of the free $N^3H$ group, liberation of the $N^1H$ function and transformation of the radical $A^1$ into the radical R. If enantiomerically pure compounds of the formula I in which $R^3$ has the meaning hydrogen are to be prepared and if the enantiomeric separation is carried out at the stage of the compounds of the formula V, the compounds of the formula V can be reacted again according to methods known from the literature, e.g. according to M.J.O. Anteunis et al., Bull. Soc. Chim. Belg. 96 (1987), 459, to give the hydantoins of the formula III, with which the subsequent reactions mentioned are then carried out.

Compounds of the formula I in which X or $X^1$ have a meaning other than hydrogen are obtainable from or analogously to the compounds unsubstituted in the amino, amidino and guanidino group according to standard methods, for example by acylation, or alkylation of the unsubstituted compounds or by reacting compounds of the formula VIII, for example, with hydroxylamine instead of ammonia.

Compounds of the formula I which are enantiomerically pure with respect to the asymmetric center in the hydantoin ring can be prepared, for example, by resolution of the compounds of the formula V, for example by crystallization of the salts with R-mandelic acid or S-mandelic acid, and conversion of the enantiomerically pure compounds of the formula V obtained into those of the formula I by the routes explained. Other chiral acids are also suitable for the resolution. Easily accessible or commercially available optically pure compounds are preferably employed, such as malic acid, tartaric acid, lactic acid, camphorsulfonic acid, ketopinic acid (cf., for example, Organic Syntheses, Volume 45, p. 55) or menthoxyacetic acid. Optically pure bases are also suitable for the resolution, if this is not carried out at the stage of the compounds of the formula V but at the stage of the amino acids of the formula IV and the amino group is present in a reversibly protected form. Suitable optically pure bases are, for example, 1-phenylethylamine, ephedrine, brucine, strychnine or quinine. Enantiomerically pure amino acid derivatives in which either the amino group or the carboxylic acid group is blocked are also suitable as chiral auxiliary reagents for the preparation of enantiomerically pure compounds of the formula I. Suitable amino acid derivatives which may be mentioned are pyroglutamic acid, N-acetylproline, N-formylthiazolidinecarboxylic acid, phenylglycine tert-butyl ester or valine tert-butyl ester.

In the reactions for the preparation of the compounds of the formula I, it may be appropriate to block functional groups temporarily by suitable customary protective groups which can be introduced and removed again according to methods known per se (see, for example, the references indicated above). For example, guanidino groups can be blocked by $NO_2$ or Mtr protective groups. Amino groups which are not involved in the reaction can be present, for example, in protected form as Boc or Z derivatives. Amino group protection is unnecessary if the amino groups to be generated are still present as nitro or cyano groups and are only produced after the reaction, e.g. by hydrogenation. Carboxyl groups not involved in the reaction are preferably protected as $(C_1-C_6)$-alkyl esters, in particular tert-butyl esters, or as benzyl esters. After the reaction, the protective groups present are removed in a suitable manner, for example nitro groups (guanidino protection), benzyloxycarbonyl groups and benzyl esters are removed by hydrogenation, protective groups of the tert-butyl type are cleaved by acid or 9-fluorenylmethoxycarbonyl radicals are removed by secondary amines.

Route B:

Compounds of the formula I can also be prepared by reacting compounds of the formula IX

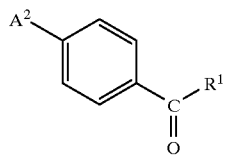

(IX)

in which $A^2$ is halogen, preferably bromine, nitro or cyano and $R^1$ has the meanings indicated above, under the known conditions of the Strecker reaction to give the aminonitriles of the formula X

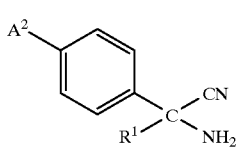
(X)

from which after hydrolysis of the aliphatic nitrile group following methods known from the literature (see, for example, D. Dopp and H. Dopp in Methoden der organischen Chemie [Methods of organic chemistry] (Houben-Weyl), Thieme-Verlag, Stuttgart 1985, 4th Edition, Volume E5, p. 1024 ff., or F. Becke, H. Fleig and P. Päβler, Liebigs Ann. Chem. 749 (1971), 198), e.g. with concentrated mineral acids, such as conc. hydrochloric acid or conc. sulfuric acid, or a mixture of hydrochloric acid and formic acid, the carboxamides of the formula XI

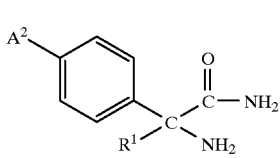
(XI)

are obtained. These can be reacted, as explained under Route A, with isocyanatoacetic acid esters of the formula VI to give compounds of the formula XII

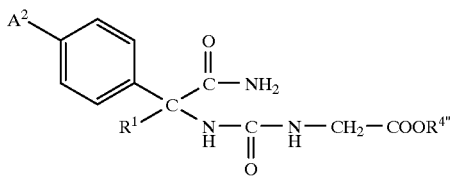
(XII)

in which $R^{4'''}$ has the meanings indicated under Route A and from which, by cyclization analogously to the details under Route A, compounds of the formula XIII

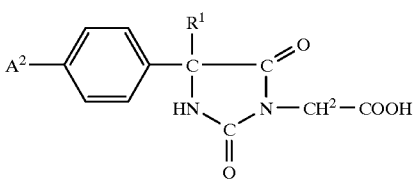
(XIII)

are obtained, which can be converted into compounds of the formula I as described under A.

Compounds of the formula I in which $R^3$ has the meaning hydrogen can be prepared by cyclizing the compounds of the formula XI analogously to methods known from the literature, e.g. as described in EP-A-173522 using dimethyl carbonate or by benzyloxycarbonylation of the amino group oin the 2-position and subsequent treatment with a base, to give the hydantoins of the formula XIV

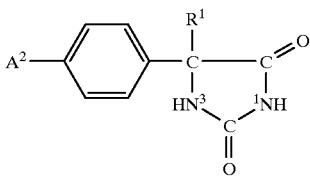
(XIV)

If desired, substituents can then be introduced into the 3-position of the hydantoin analogously to the details under Route A, by protection of the $N^1H$ function, alkylation, cycloalkylation, arylation or aralkylation of the $N^3H$ group and liberation of the $N^1H$ function and/or, analogously to the details under Route A, compounds of the formula I can be obtained by transformation of the radical $A^2$ into the radical R.

Otherwise, the explanations given under Route A correspondingly apply, for example for the introduction of substituents X on the amino, amidino and guanidino groups or for the use of protective groups in the reaction steps. Compounds of the formula I which are enantiomerically pure with respect to the asymmetric center in the hydantoin ring can be prepared by the Route B, e.g. by resolution of the compounds of the formula XI, for example by crystallization of the salts with D-tartaric acid or L-tartaric acid, and conversion of the enantiomerically pure compounds of the formula XI obtained into those of the formula I by the routes explained. Other chiral acids are also suitable for the resolution, for example those indicated above under Route A, including the amino acids haylng a blocked amino group mentioned there.

Route C:

It is also possible to obtain compounds of the formula I by reacting compounds of the formula IX in which $A^2$ and $R^1$ have the meanings indicated there according to the details under Route A under the conditions of the Bucherer reaction to give the hydantoins of the formula XIV

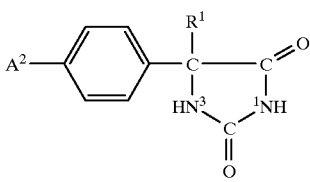
(XIV)

and alkylating these on the $N^1H$ function using a haloacetic acid ester, for example methyl chloroacetate, according to known methods. The compounds obtained of the formula XV

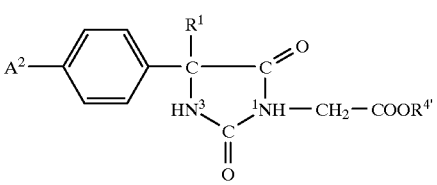
(XV)

in which $R^{4'}$ as above can have the meanings indicated for $R^4$ with the exception of hydrogen, can be converted into the desired compounds of the formula I according to the above details by introduction of an alkyl, cycloalkyl, aryl or aralkyl substituent on the N³H function and/or transformation of the radical A² into the radical R and/or hydrolysis of the carboxylic ester group.

The compounds of the formula I are advantageously suitable as intermediates for the preparation of the pharmaceutical active compounds inhibiting cell-cell adhesion described in the German Patent Applications P 43 48 944 and P 44 27 979 and the PCT Application PCT/EP 94/03491, if these contain, as an N-terminal component, a 2,5-dioxoimidazolidine ring which is linked to a substituted or unsubstituted amino or aminomethyl, amidino or guanidino group yla a 1,4-phenylene unit, in particular if active compounds are to be prepared which are to be enantiomerically pure with respect to the asymmetric center in the hydantoin ring. Separation of the isomers can be carried out at various stages of the active compound preparation, depending on the C-terminal component of the active compound, however, it may be particularly favorable to employ the compounds of the formula I in the active compound synthesis in enantiomerically pure form with respect to the asymmetric center in the hydantoin ring in order that, for example, half of the substance is not lost from the valuable C-terminal component.

The linkage of the compounds of the formula I representing the N-terminal component of the active compounds to a further component of the active compound molecule or to the complete C-terminal component can be carried out according to customary methods. Compounds of the formula I in which $R^3$ has the meaning $CH_2COOR^4$ can be reacted, for example, to give the subsequent stage according to coupling methods of peptide chemistry known per se to the person skilled in the art (see, for example, Houben-Weyl, Methoden der organischen Chemie [Methods of organic chemistry], Volume 15/1 and 15/2, Stuttgart 1974) if the compound of the formula I is to be linked yla an amino group of the further component or the complete C-terminal component. If a compound of the formula I in which $R^3$ has the meaning $CH_2COOH$ is to be condensed with an amino group, then as a rule an activation of the carboxylic acid group is first carried out, e.g. by conversion into an acid chloride, into an activated ester or into a mixed anhydride or by reaction with coupling reagents such as carbodiimides, e.g. DCC (dicyclohexylcarbodiimide), or TOTU (O-(cyano-ethoxycarbonylmethylene)amino)-N, N-N', N'-tetramethyluronium tetrafluoro-borate), where it may be advantageous, beside the actual activating agents, to add further customary auxiliaries during the activation of the carboxylic acid group with DCC, for example 1-hydroxybenzotriazole (HOBt). In these linkage reactions, it may be appropriate first to protect functional groups by protective groups (for this purpose see the above explanations for protective groups).

With respect to the pharmaceutical active compounds for which the compounds of the formula I can serve as intermediates, reference is made here to the German Patent Applications P 43 38 944 and P 44 27 979 and the PCT Application PCT/EP 94/03491, which in this respect are fully part of the present disclosure. A group of these active compounds which may be mentioned by way of example, without a restriction being associated therewith, are the compounds of the formula XVI

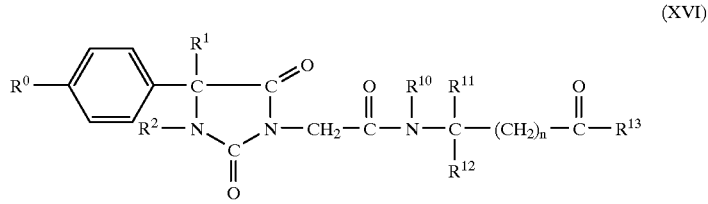

(XVI)

in which
$R^0$ is $C(=NH)-NH-X$, $CH_2-NH-X$ or $NH-X^1$;
X is hydrogen, $(C_1-C_6)$-alkyl, $(C_1-C_6)$-alkylcarbonyl, $(C_1-C_6)$-alkoxycarbonyl, $(C_1-C_{18})$-alkylcarbonyloxy-$(C_1-C_6)$-alkoxycarbonyl, optionally substituted $(C_6-C_{14})$-arylcarbonyl, optionally substituted $(C_6-C_{14})$-aryloxycarbonyl, $(C_6-C_{14})$-aryl-$(C_1-C_6)$-alkoxycarbonyl which can also be substituted in the aryl radical, $(R^5O)_2P(O)$, cyano, hydroxyl, $(C_1-C_6)$-alkoxy, $(C_6-C_{14})$-aryl-$(C_1-C_6)$-alkoxy which can also be substituted in the aryl radical, or amino;
$X^1$ has one of the meanings of X or is R'—NH—C(=N—R"), where R' and R" independently of one another have the meanings of X;
$R^1$ is $(C_1-C_8)$-alkyl, $(C_6-C_{14})$-aryl-$(C_1-C_8)$-alkyl optionally substituted in the aryl radical or $(C_3-C_8)$-cycloalkyl;
$R^2$, $R^{10}$ and $R^{11}$ independently of one another are hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical or $(C_3-C_8)$-cycloalkyl;
$R^5$ is hydrogen, $(C_1-C_8)$-alkyl, optionally substituted $(C_6-C_{14})$-aryl or $(C_6-C_{14})$-aryl-$(C_1eC_8)$-alkyl which can also be substituted in the aryl radical;
$R^{12}$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical, $(C_3-C_8)$-cycloalkyl or 2-, 3- or 4-pyridyl;
$R^{13}$ is hydroxyl, $(C_1-C_{18})$-alkoxy, $(C_6-C_{14})$-aryl-$(C_1-C_8)$-alkoxy which can also be substituted in the aryl radical, optionally substituted $(C_6-C_{14})$-aryloxy, amino or mono- or di($C_1-C_{18}$-alkyl)amino;
n is an integer from 0 to 6.

Preferably, when using the compounds of the formula I as intermediates, active compounds of the formula XVI are prepared in which one or more of the radicals have preferred meanings and/or in which a uniform configuration, particularly preferably the S configuration, is present with respect to the asymmetric center in the hydantoin ring. If $R^{11}$ and $R^{12}$ are different, then the carbon atom carrying these radicals is also an asymmetric center. It is preferred if a uniform configuration, particularly preferably the S configuration, is also present at this center. $R^0$ is preferably $C(=NH)-NH-X$, and for the preferred meanings of the radicals X, $R^1$ and $R^2$ the information given above also applies. $R^{10}$ is preferably hydrogen, $(C_1-C_6)$-alkyl or benzyl, particularly preferably hydrogen. $R^{11}$ is preferably hydrogen or $(C_1-C_8)$-alkyl, particularly preferably hydrogen. $R^{12}$ is preferably optionally substituted $(C_6–C_{14})$-aryl or pyridyl, particularly preferably optionally substituted phenyl, very particularly preferably unsubstituted phenyl. $R^{13}$ is preferably hydroxyl or $(C_1–C_8)$-alkoxy, particularly preferably $(C_1–C_4)$-alkoxy. n is preferably an integer from 0 to 3, particularly preferably the numbers 1 or 2, very particularly preferably the number 1.

The preparation of the active compounds of the formula XVI mentioned by way of example from the compounds of the formula I, in particular those in which $R^3$ has the meaning $CH_2COOH$, can be carried out according to the above illustrations by reacting these according to coupling methods of peptide chemistry known per se to the person skilled in the art with compounds of the formula XVII

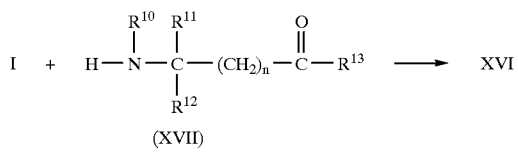

(XVII)

in which $R^{10}$ to $R^{13}$ and n have the meanings indicated for the formula XVI.

The preparation of the active compounds can also be carried out, however, by first—as already explained—reacting compounds of the formula I in which $R^3$ has the meaning hydrogen with a haloacetic acid ester and condensing the product obtained or the free acid prepared therefrom with the compounds of the formula XVII. The compounds of the formula I do not always have to be the direct precursors of the desired active compounds, but after the reaction with the compounds of the formula I one or more further reaction steps can additionally follow on the route to the active compound. Depending on the structure of the C-terminal part of the active compound, it may be favorable to synthesize the active compound in several steps from the N-terminal end, i.e. to say on the compound of the formula I.

If compounds of the formula I in which R is an unsubstituted or substituted amino or aminomethyl, amidino or guanidino group are linked with the complete C-terminal component of the active compound, then the active compound is obtained in one step from the compounds of the formula I. However, it may also be favorable first to link compounds of the formula I in which R is cyano, i.e. compounds of the formula Ib (Ib)

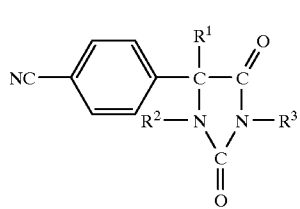

in which $R^1$, $R^2$ and $R^3$ have the meanings indicated above, to the complete C-terminal component of the active compound and in the last step of the active compound preparation then to convert the cyano group into the aminomethyl or amidino group of the active compound according to the methods known per se already explained above. In the case of the active compounds of the formula XVI mentioned by way of example in which $R^0$ has the meaning $C(=NH)—NH—X$ or $CH_2—NH—X$, it is possible in this procedure, for example, for a compound of the formula Ib in which $R^3$ has the meaning $CH_2COOR^4$ to be reacted with a compound of the formula XVII and the product initially obtained then to be converted into an aminomethyl or amidino group in the active compound by transformation of the cyano group.

The present invention also relates to the compounds, obtained in this procedure and likewise being intermediates or alternatively direct precursors for the active compounds, of the formula XVIII (XVIII)

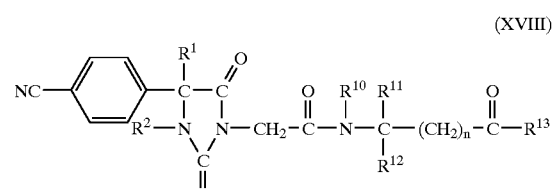

in which
$R^1$ is $(C_1–C_8)$-alkyl, $(C_6–C_{14})$-aryl-$(C_1–C_8)$-alkyl optionally substituted in the aryl radical or $(C_3–C_8)$-cycloalkyl;
$R^2$, $R^{10}$ and $R^{11}$ independently of one another are hydrogen, $(C_1–C_8)$-alkyl, optionally substituted $(C_6–C_{14})$-aryl, $(C_6–C_{14})$-aryl-$(C_1–C_8)$-alkyl optionally substituted in the aryl radical or $(C_3-C_8)$-cycloalkyl;
$R^{12}$ is hydrogen, $(C_1–C_8)$-alkyl, optionally substituted $(C_6–C_{14})$-aryl, $(C_6–C_{14})$-aryl-$(C_1–C_8)$-alkyl optionally substituted in the aryl radical, $(C_3–C_8)$-cycloalkyl or 2-, 3- or 4-pyridyl;
$R^{13}$ is hydroxyl, $(C_1–C_{18})$-alkoxy, $(C_6–C_{14})$-aryl-$(C_1–C_8)$-alkoxy which can also be substituted in the aryl radical, optionally substituted $(C_6–C_{14})$-aryloxy, amino or mono- or di($C_1–CI_8$)-alkyl)amino;
n is an integer from 0 to 6, and their salts.

The above explanations also apply here with respect to the alkyl and aryl substituents etc. All stereoisomers and all mixtures of stereoisomeric forms are also included here. The asymmetric centers in the hydantoin ring and on the carbon atoms carrying the groups $R^{11}$ and $R^{12}$ can be present independently of one another in the R configuration or S configuration in each case.

The above details in turn apply to the preferred meanings of the substituents in the formula XVIII. Preferably, a uniform configuration is present at the asymmetric center in the hydantoin ring and also at the carbon atom carrying the groups $R^{11}$ and $R^{12}$, particularly preferably the S configuration at both. Preferred compounds of the formula XVIII are those in which
$R^1$ is $(C_1–C_4)$-alkyl, cyclopropyl or benzyl, particularly preferably methyl;
$R^2$ is hydrogen or $(C_1–C_4)$-alkyl, particularly preferably hydrogen;
$R^{10}$ is hydrogen, $(C_1–C_6)$-alkyl or benzyl, particularly preferably hydrogen;
$R^{11}$ is hydrogen or $(C_1–C_8)$-alkyl, particularly preferably hydrogen;
$R^{12}$ is optionally substituted $(C_6–C_{14})$-aryl or pyridyl, particularly preferably optionally substituted phenyl, very particularly preferably unsubstituted phenyl;
$R^{13}$ is hydroxyl or $(C_1–C_8)$-alkoxy, particularly preferably $(C_1–C_4)$-alkoxy;
n is an integer from 0 to 3, particularly preferably the numbers 1 or 2, very particularly preferably the number 1.

Moreover, preferred compounds of the formula XVIII are those in which a uniform configuration is present at the asymmetric center in the hydantoin ring and also at the carbon atom carrying the radicals $R^{11}$ and $R^{12}$, in particular the S configuration at both.

The preparation of the compounds of the formula XVIII can be carried out, for example, as already explained above by coupling the compounds of the formula Ib in which $R^3$ has the meaning $CH_2$—COOH to compounds of the formula XVII according to the customary coupling methods of peptide chemistry known per se to the person skilled in the art, e.g. with the aid of reagents such as carbodiimides, e.g. DCC, or, for example, with TOTU. The conversion of the cyano group into the group contained in the active compound haylng cell-cell adhesion-inhibiting, in particular platelet aggregation-inhibiting action, e.g. in particular into the amidino group, and if desired its derivatives substituted by the radical X or its salts can, as likewise already explained, also be carried out according to the customary methods known for this conversion to the person skilled in the art, in the case of the amidino group, for example, by reaction of the cyano group with hydroxylamine to give the amidoxime group and subsequent hydrogenation (see, for example, Tetrahedron 42 (1986), 5869) or by addition of an alcohol to the cyano group in anhydrous medium and ammonolysis of the imino ester group.

EXAMPLES

The products were identified by means of mass spectra andlor NMR spectra.

Example 1

(S)-(4-(4-Cyanophenyl)-4-methyl-2,5-dioxoimidazolidin-1-yl)acetic acid 1a. (R S)-4-(4-Bromophenyl)-4-methyl-2,5-dioxoimidazolidine 49.8 g (0.25 mol) of 4-bromoacetophenone, 21.2 g (0.325 mol) of potassium cyanide and 211.4 g (2.2 mol) of ammonium carbonate were suspended in 1.0 l of an aqueous ethanol solution (0.5 l of distilled water and 0.5 l of ethanol). The suspension was stirred at 60° C. until starting material could no longer be detected by thin-layer chromatography (8 hours). The mixture was allowed to cool to room temperature. The pH of the solution was adjusted to pH =6.3 using half-concentrated hydrochloric acid. The product deposited as a white precipitate. The mixture was allowed to stand overnight at 4° C. The white precipitate was filtered off with suction, washed with water and dried in vacuo over phosphorus pentoxide.

Yield: 65.3 g of a white solid (97%).
FAB-MS: 269 $(M+H)^+$ 1 b. (R S)-2-Amino-2-(4-bromophenyl )propionic acid 5.3 g (20 mmol) of (R,S)-4-(4-bromophenyl)-4-methyl-2,5-dioxoimid-azolidine were suspended in 50 ml of 3N sodium hydroxide solution.The suspension was heated in an autoclave for 1 hour at 145° C. under a nitrogen overpressure of 10 bar. The cooled reaction solution was diluted with 150 ml of water and, with ylgorous stirring, brought to a pH of 4 with ice cooling using acetic acid. It was stirred at 0° C. for 2 hours. The precipitate was filtered off with suction, washed with water and dried in vacuo over phosphorus pentoxide.

Yield: 3.65 g of a white solid (75%).
FAB-MS: 244 $(M+H)^+$ 1 c. Ethyl (R,S)-2-amino-2-(4-bromophenyl)propionate 27.3 g (112.3 mmol) of (R,S)-2-amino-2-(4-bromophenyl) propionic acid were suspended in 150 ml of 9.8N ethanolic hydrogen chloride solution.

The mixture was refluxed for 18 hours, 50 ml of 9.8N ethanolic hydrogen chloride solution were again added and it was refluxed for a further 5 hours. The solution was concentrated and the residue was partitioned between ethyl acetate and saturated sodium bicarbonate solution. The organic phase was washed with water and dried over sodium sulfate. The crude product (23.22 g) was distilled in a high vacuum for purification (b.p.=129–130° C. at 2 torr).

Yield: 20.7 g (68%).
FAB-MS: 272 $(M+H)^+$

1d. Ethyl (S)-2-amino-2-(4-bromophenyl)propionate 44.3 g (163 mmol) of ethyl (R,S)-2-amino-2-(4-bromophenyl)propionate and 24.8 g of D-(-)mandelic acid (163 mmol) were dissolved in 138 ml of isopropanol at room temperature. 414 ml of diisopropyl ether were added and the mixture was cooled overnight at 0° C. The deposited precipitate was filtered off with suction. The salt obtained was additionally recrystallized a further two times in the same manner. 20 g of enantiomerically pure salt were obtained ($[\alpha]D=-14°$ (c =1; 2.15N ethanolic hydrogen chloride solution-, 22° C.). The salt was partitioned between ethyl acetate and aqueous sodium bicarbonate solution. The organic phase was washed with water, dried over magnesium sulfate and concentrated in vacuo. The enantiomeric purity was determined by HPLC to be greater than 99% ee after derivatization with R(-)-α-methoxy-α-(trifluoromethyl)phenylacetyl chloride (Mosher reagent).

Yield: 12.5 g (28%).
$[\alpha]D=+52.7°$ (c=1; 2.15N ethanolic hydrogen chloride solution; 22° C.).
FAB-MS: 272 $(M+H)^+$ 1e. N-((S)-1 -(4-Bromophenyl)-1 -(ethoxycarbonyl)ethyl)-N'-(ethoxy-carbonylmethyl)urea 12.4 g (45.6 mmol) of ethyl (S)-2-amino-2-(4-bromophenyl)propionate were dissolved in 70 ml of methylene chloride. A solution of 5.11 ml (45.6 mmol) of ethyl isocyanatoacetate in 35 ml of methylene chloride was added dropwise at 0° C. in the course of 15 minutes. The mixture was stirred for 2 hours at 0° C. and then concentrated.

Yield: 18.1 g (99%).
$[\alpha]D=+10.7°$ (c=1; 2.15N ethanolic hydrogen chloride solution; 22° C.).
FAB-MS: 401 $(M+H)^+$ 1f. (S)-(4-(4-Bromophenyl)-4-methyl-2,5-dioxoimidazolidin-1-yl)acetic acid 18 g (44.9 mmol) of N-((S)-1-(4-bromophenyl)-1-(ethoxycarbonyl)ethyl)-N'-(ethoxycarbonylmethyl)urea were treated with 180 ml of 6N hydrogen chloride solution. The reaction mixture was heated to boiling under reflux for 10 hours. It was allowed to cool to 0° C. and the precipitated reaction product was filtered off with suction. It was washed with water and dried in vacuo over phosphorus pentoxide.

Yield: 11.4 g (78%).
$[\alpha]D=+32.8°$ (c=1; 2.15N ethanolic hydrogen chloride solution; 22° C.).
FAB-MS: 327 $(M+H)^+$ 1g. (S)-(4-(4-Cyanophenyl)-4-methyl-2,5-dioxoimidazolidin-1-yl)acetic acid 11.75 g (35.9 mmol) of (S)-(4-(4-bromophenyl)-4-methyl-2,5-dioxoimid-azolidin-1-yl)acetic acid were dissolved in 90 ml of dimethylformamide. 14.15 g (158 mmol) of copper(l) cyanide were added and the mixture was refluxed for 20 hours with stirring. The reaction mixture was cooled and then poured into 300 ml of water. The aqueous phase was rendered acidic using concentrated hydrochloric acid (pH =1–1.5), stirred for 30 minutes and filtered off with suction through a Seitz layer. The aqueous phase was extracted three times with ethyl acetate. The combined organic phases were washed with water, dried over magnesium sulfate and concentrated in vacuo.

Yield: 9.3 g (95%).
$[\alpha]D=+33.4°$ (c=1; 2.15N ethanolic hydrogen chloride solution; 22° C.).
FAB-MS: 274 (M+H)$^+$

Example 2

(R)-(4-(4-Cyanophenyl)-4-methyl-2,5-dioxoimidazolidin-1-yl)acetic acid (R)-(4-(4-Cyanophenyl)-4-methyl-2,5-dioxomidazolidin-1-yl)acetic acid was obtained analogously to Example 1. For this purpose, the resolution of ethyl (R,S)-2-amino-2-(4-bromophenyl)propionate was carried out as in Example 1d, but using L-(+)-mandelic acid instead of D-(-)mandelic acid. The ethyl (R)-2-amino-2-(4-bromophenyl)propionate obtained was then reacted further analogously to Example 1e–g.

FAB-MS: 274 (M+H)$^+$

Example 3

Methyl (S)-(4-(4-cyanophenyl)-4-methyl-2,5-dioxoimidazolidin-1-yl)-acetate

FAB-MS: 288 (M+H)$^+$

Example 4

Methyl (R)-(4-(4-cyanophenyl)-4-methyl-2,5-dioxoimidazolidin-1-y)-acetate

FAB-MS: 288 (M+H)$^+$

Example 5

(S)-(4-(4-Amino-imino-methyl)phenyl)-4-methyl-2,5-dioxoimidazolidin-1-yl)acetic acid hydrochloride 5a. Ethyl (S)-(4-(4-(ethoxy-imino-methyl)phenyl)-4-methyl-2,5-dioxoimid-azolidin-1-yl)acetate hydrochloride A solution of 27.3 g of (S)-(4-(4-cyanophenyl)-4-methyl-2,5-dioxoimid-azolidin-1-yl)acetic acid (100 mmol) in 400 ml of absolute ethanol was cooled to 0° C. Dry hydrogen chloride gas was passed into the solution, the temperature always being kept below 10° C., until the nitrile band was no longer present in the IR spectrum. The ethanolic solution was concentrated.

Yield: 38.1 g (99%).
FAB-MS: 348 (M+H)$^+$

5b. Ethyl (S)-(4-(4-(amino-imino-methyl)phenyl)-4-methyl-2,5-dioxoimid-azolidin-1-yl) acetate hydrochloride 38 g of ethyl (S)-(4-(4-(ethoxy-imino-methyl)phenyl)-4-methyl-2,5-dioxoimid-azolidin-1-yl)acetate hydrochloride (99 mmol) were suspended in 380 ml of isopropanol and treated with 115 ml of a 2N solution of ammonia in isopropanol. The reaction mixture was stirred for 2 hours at 50° C. The mixture was cooled and then treated with 2 l of diethyl ether. The precipitate was filtered off with suction and dried in a high vacuum.

Yield: 24.8 g (71%).
$[\alpha]D=+33.1°$ (c=1; 2.15N ethanolic hydrogen chloride solution; 22° C.).
FAB-MS: 319 (M+H)$^+$ 5c. (S)-(4-(4-(Amino-imino-methyl)phenyl)-4-methyl-2,5-dioxoimid-azolidin-1-yl)acetic acid hydrochloride 24.7 g of ethyl (S)-(4-(4-(amino-imino-methyl)phenyl)-4-methyl-2,5-dioxoimidazolidin-1-yl)acetate hydrochloride (69.7 mmol) were dissolved in 375 ml of concentrated hydrochloric acid. The solution was heated to boiling for 6 hours and then concentrated. The residue was dissolved in water and freeze-dried.

Yield: 21.65 g (95%).
$[\alpha]D=+42.7°$ (c=1; 1 N hydrochloric acid; 22° C.).
FAB-MS: 291 (M+H)$^+$

Example 6

(R)-(4-(4-(Amino-imino-methyl)phenyl)-4-methyl-2,5-dioxoimidazolidin-1-yl)acetic acid hydrochloride The preparation of (R)-(4-(4-(amino-imino-methyl)phenyl)-4-methyl-2,5-dioxoimidazolidin-1-yl)acetic acid was carried out starting from (R)-(4-(4-(cyanophenyl)-4-methyl-2,5-dioxoimidazolidin-1-yl)acetic acid analogously to Example 5.

$[\alpha]D=+42.7°$ (c=1; 1N hydrochloric acid; 22° C.).
FAB-MS: 291 (M+H)$^+$

Example 7

Methyl (S)-(4-(4-(amino-imino-methyl)phenyl)-4-methyl-2,5-dioxoimid-azolidin-1-yl)acetate hydrochloride

FAB-MS: 305 (M+H)$^+$

Example 8

Methyl (R)-(4-(4-(amino-imino-methyl)phenyl )-4-methyl-2,5-dioxoimid-azolidin-1-yl)acetate hydrochloride

FAB-MS: 305 (M+H)$^+$

Example 9

Benzyl (S)-(4-(4-(amino-imino-methyl)phenyl)-4-methyl-2,5-dioxoimid-azolidin-1-yl)acetate hydrochloride

FAB-MS: 381 (M+H)$^+$

Example 10

Benzyl (R)-(4-(4-(amino-imino-methyl)phenyl)-4-methyl-2,5-dioxoimid-azolidin-1-yl)acetate hydrochloride

FAB-MS: 381 (M+H)$^+$

Example 11 tert-Butyl (S)-(4-(4-(amino-imino-methyl)phenyl)-4-methyl-2,5-dioxoimidazolidin-1-yl) acetate hydrochloride

FAB-MS: 347 (M+H)$^+$

Example 12 tert-Butyl (R)-(4-(4-(amino-imino-methyl)phenyl)-4-methyl-2,5-dioxo-imidazolidin-1-yl)acetate hydrochloride

FAB-MS: 347 (M+H)$^+$

Example 13

(S)-(4-(4-(Benzyloxycarbonylamino-imino-methyl)-phenyl)-4-methyl-2,5-dioxoimidazolidin-1-yl)acetic acid

FAB-MS: 425 (M+H)$^+$

Example 14

(R)-(4-(4-(Benzyloxycarbonylamino-imino-methyl) phenyl)-4-methyl-2,5-dioxoimidazolidin-1-yl)acetic acid

FAB-MS: 425 (M+H)$^+$

Example 15

(S)-4-(4-(Amino-imino-methyl)phenyl)-4-methyl-2, 5-dioxoimidazolidine hydrochloride

FAB-MS: 233 (M+H)$^+$

Example 16

(R)-4-(4-(Amino-imino-methyl)phenyl)-4-methyl-2, 5-dioxoimidazolidine hydrochloride

FAB-MS: 233 (M+H)$^+$

Example 17

(S)-(4-(4-(Aminomethyl)phenyl)-4-methyl-2,5-dioxoimidazolidin-1-yl)acetic acid

FAB-MS: 278 (M+H)$^+$

Example 18

(R)-(4-(4-(Aminomethyl)phenyl)-4-methyl-2,5-dioxoimidazolidin-1-yl)acetic acid

FAB-MS: 278 (M+H)$^+$

Example 19

(S)-(4-(4-(tert-Butoxycarbonylaminomethyl)phenyl )- 4-methyl-2,5-dioxoimidazolidin-1-yl)acetic acid

FAB-MS: 378 (M+H)$^+$

Example 20

(R)-(4-(4-(tert-Butoxycarbonylaminomethyl )-phenyl)-4-methyl-2,5-dioxoimidazolidin-1-yl)acetic acid

FAB-MS: 378 (M+H)$^+$

Example 21

(S)-(4-(4-Guanidinophenyl)-4-methyl-2,5-dioxoimidazolidin-1-yl)acetic acid

FAB-MS: 306 (M+H)$^+$

Example 22

(R)-(4-(4-Guanidinophenyl)-4-methyl-2,5-dioxoimidazolidin-1-yl)acetic acid

FAB-MS: 306 (M+H)$^+$

Example 23

(S)-(4-(4-(Benzyloxycarbonylguanidino)phenyl)-4-methyl-2,5-dioxo-imidazolidin-1-yl)acetic acid

FAB-MS: 440 (M+H)$^+$

Example 24

(R)-(4-(4-(Benzyloxycarbonylguanidino)phenyl)-4-methyl-2,5-dioxo-imidazolidin-1-yl)acetic acid

FAB-MS: 440 (M+H)$^+$

Example 25

(S)-(4-(4-(Amino-imino-methyl)phenyl)-4-ethyl-2,5-dioxoimidazolidin-1-yl)acetic acid

FAB-MS: 305 (M+H)$^+$

Example 26

(R)-(4-(4-(Amino-imino-methyl)phenyl)-4-ethyl-2, 6-dioxoimidazolidin-1-yl)acetic acid

FAB-MS: 305 (M+H)$^+$

Example 27

(S)-($^4$-($^4$-(Amino-imino-methyl)phenyl)-4-cyclopropyl-2,5-dioxo-imidazolidin-1-yl)acetic acid

FAB-MS: 317 (M+H)$^+$

Example 28

(R)-(4-(4-(Amino-imino-methyl)phenyl)-4-cyclopropyl-2,5-dioxo-imidazolidin-1-yl)acetic acid

FAB-MS: 317 (M+H)$^+$

Example 29

(S)-($^4$-($^4$-(Amino-imino-methyl)phenyl)-4-tert-butyl-2,5-dioxo-imidazolidin-1-yl)acetic acid

FAB-MS- 333 (M+H)$^+$

Example 30

(R)-($^4$-($^4$-(Amino-imino-methyl)phenyl)-4-tert-butyl-2,5-dioxo-imidazolidin-1-yl)acetic acid

FAB-MS: 333 (M+H)$^+$

Example 31

(S)-(4-(4-(Amino-imino-methyl)phenyl)-4-benzyl-2, 5-dioxoimidazolidin-1-yl)acetic acid

FAB-MS: 367 (M+H)$^+$

Example 32

(R)-(4-(4-(Amino-imino-methyl)phenyl)-4-benzyl-2, 5-dioxoimidazolidin-1-yl)acetic acid

FAB-MS: 367 (M+H)$^+$

Example 33

(S)-(4-(4-(Amino-imino-methyl)phenyl)-3,4-dimethyl-2,5-dioxo-imidazolidin-1-yl)acetic acid hydrochloride 33a. Methyl (S)-(4-(4-cyanophenyl)-3,4-dimethyl-2,5-dioxoimidazolidin-1-yl)acetate 3 g of methyl (S)-(4-(4-cyanophenyl)-4-methyl-2,5-dioxoimidazolidin-1-yl)acetate (10.4 mmol) were dissolved in 15 ml of anhydrous dimethylformamide under argon. 11.4 mmol of sodium hydride in the form of a dispersion in mineral oil were added in an argon countercurrent. The reaction mixture was stirred at room temperature for 15 minutes. It was then treated with 721 μl of methyl iodide (11.4 mmol). The mixture was stirred at room temperature for 4 hours and then allowed to stand at room temperature overnight. The solution was concentrated. For purification, the substance was chromatographed on silica gel using methylene chloride/ethyl acetate (9.5:0.5). The fractions containing the pure substance were concentrated.

Yield: 2.14 g of oil (68%).
FAB-MS: 302 (M+H)+

33b. Methyl (S)-(4-(4-(ethoxy-imino-methyl)phenyl)-3,4-dimethyl-2,5-dioxo-imidazolidin-1-yl)acetate hydrochloride A solution of 2.56 g of methyl (S)-(4-(4-cyanophenyl)-3,4-dimethyl-2,5-dioxoimidazolidin-1-yl)acetate (8.5 mmol) in 40 ml of absolute ethanol was cooled to 0° C. Dry hydrogen chloride gas was passed into the solution, the temperature always being kept below 10° C., until the nitrile band was no longer present in the IR spectrum. The ethanolic solution was concentrated to 20 ml and treated with 200 ml of diethyl ether. The suspension was concentrated and dried in a high vacuum.

Yield: 2.27 g (76%).
FAB-MS- 348 (M+H)+

33c. Methyl (S)-(4-(4-(amino-imino-methyl)phenyl)-3,4-dimethyl-2,5-dioxo-imidazolidin-1-yl)acetate hydrochloride 2.26 g of methyl (S)-(4-(4-(ethoxy-imino-methyl)phenyl)-3,4-dimethyl-2,5-dioxoimidazolidin-1-yl)acetate hydrochloride (6.4 mmol) were suspended in 25 ml of isopropanol and treated with 7.2 ml of a 2N solution of ammonia in isopropanol. The reaction mixture was stirred at 50° C. for 2.5 hours. The mixture was cooled and then treated with 200 ml of diethyl ether. The precipitate was filtered off with suction and dried in a high vacuum.

Yield: 1.03 g (45%).
FAB-MS: 319 (M+H)+

33d. (S)-(4-(4-(Amino-imino-methyl)phenyl)-3,4-dimethyl-2,5-dioxoimid-azolidin-1-yl)acetic acid hydrochloride 1 g of methyl (S)-(4-(4-(amino-imino-methyl)phenyl)-3,4-dimethyl-2,5-dioxo-imidazolidin-1-yl)acetate hydrochloride (2.8 mmol) was dissolved in 20 ml of concentrated hydrochloric acid. The solution was heated to boiling for 6 hours and then concentrated.

Yield: 770 mg (81%)
FAB-MS: 305 (M+H)+

Example 34

(R)-(4-(4-(Amino-imino-methyl)phenyl)-3,4-dimethyl-2,5-dioxoimid-azolidin- 1-yl)acetic acid hydrochloride The preparation of (R)-(4-(4-(amino-imino-methyl)phenyl)-3,4-dimethyl-2,5-dioxoimidazolidin-1-yl)acetic acid hydrochloride was carried out starting from (R)-(4-(4-cyanophenyl)-4-methyl-2,5-dioxoimidazolidin-1-yl)acetic acid analogously to Example 33.

FAB-MS: 305 (M+H)+

Example 35

(S)-(4-(4-(Amino-imino-methyl)phenyl)-3-ethyl-4-methyl-2,5-dioxoimid-azolidin-1-yl)acetic acid

FAB-MS: 319 (M+H)+

Example 36

(R)-($^4$-($^4$-(Amino-imino-methyl)phenyl)-3-ethyl-4-methyl-2,5-dioxoimid-azolidin-1-yl)acetic acid

FAB-MS: 319 (M+H)+

Example 37

(S)-($^4$-($^4$-(Amino-imino-methyl)phenyl)-3-benzyl-4-methyl-2,5-dioxoimid-azolidin-1-yl)acetic acid

FAB-MS: 381 (M+H)+

Example 38

(R)-($^4$-($^4$-(Amino-imino-methyl)phenyl)-3-benzyl-4-methyl-2,5-dioxoimid-azolidin-1-yl)acetic acid

FAB-MS: 381 (M+H)+

Example 39

(S)-(4-(4-(Amino-imino-methyl)phenyl)-3-pentafluorobenzyl-4-methyl-2,5-dioxoimidazolidin-1-yl)acetic acid

FAB-MS: 471 (M+H)+

Example 40

(R)-(4-(4-(Amino-imino-methyl)phenyl)-3-pentafluorobenzyl-4-methyl-2,5-dioxoimidazolidin-1-yl)acetic acid

FAB-MS: 471 (M+H)+

Example 41

(S)-(4-(4-(Amino-imino-methyl)phenyl)-3-(4-tert-butylbenzyl)-4-methyl-2,5-dioxoimidazolidin-1-yl) acetic acid

FAB-MS: 437 (M+H)+

Example 42

(R)-(4-(4-(Amino-imino-methyl)phenyl)-3-(4-tert-butylbenzyl)-4-methyl-2,5-dioxoimidazolidin-1-yl) acetic acid

FAB-MS: 437 (M+H)+

Example 43

(S)-(4-(4-(Amino-imino-methyl )phenyl )-3-(4-nitrobenzyl)-4-methyl-2,5-dioxoimidazolidin-1-yl) acetic acid

FAB-MS: 426 (M+H)+

Example 44

(R)-(4-(4-(Amino-i mi no-methyl)phenyl)-3-(4-nitrobenzyl)-4-methyl-2,5-dioxoimidazolidin-1-yl) acetic acid

FAB-MS: 426 (M+H)+

Example 45

(S)-(4-(4-(Amino-imino-methyl)phenyl)-3-(3,5-dimethylbenzyl)-4-methyl-2,5-dioxoimidazolidin-1-yl)acetic acid

FAB-MS: 409 (M+H)+

Example 46

(R)-(4-(4-(Amino-imino-methyl)phenyl)-3-(3,5-dimethylbenzyl)-4-methyl-2,5-dioxoimidazolidin-1-yl)acetic acid

FAB-MS: 409 (M+H)+

Example 47

(S)-(4-(4-(Amino-imino-methyl)phenyl )-3-(2-naphthylmethyl)-4-methyl-2,5-dioxoimidazolidin-1-yl)acetic acid

FAB-MS: 431 (M+H)+

Example 48

(R)-(4-(4-(Amino-imino-methyl)phenyl)-3-(2-naphthylmethyl)-4-methyl-2,5-dioxoimidazolidin-1-yl)acetic acid

FAB-MS: 431 (M+H)$^+$

Example 49

(R or S)-4-(4-(Amino-imino-methyl)phenyl)-4-methyl-2,5-dioxoimid-azolidine hydrochloride
(Enantiomer I)

49a. (R,S)-2-Amino-2-(4-cyanophenyl)propionitrile 20 g (400 mmol) of sodium cyanide in 40 ml of water, 23.56 g (440 mmol) of ammonium chloride in 56 ml of warm water at 35° C. and 53.6 ml of conc. ammonia were initially introduced into a 1 liter round-bottomed flask. 58.08 g (400 mmol) of 4-cyanoacetophenone in 120 ml of 95% strength ethanol were added with stirring, and the mixture was heated at 60° C. for 5 hours and allowed to stand at room temperature overnight. The precipitate was filtered off with suction, washed with water and dried over phosphorus pentoxide in a high vacuum.

Yield: 46.1 g of pale yellow solid.

A further 5.1 g of product were obtained from the mother liquor.

Total yield: 51.2 g (75%).

FAB-MS: 172 (M+H)$^+$

The substance was reacted directly as described under 49b. without further purification.

49b. (R,S)-2-Amino-2-(4-cyanophenyl)propionamide 51.2 g (300 mmol) of (R,S)-2-amino-2-(4-cyanophenyl)propionitrile were stirred at 30° C. for 2.5 hours in 400 ml of conc. hydrochloric acid. A pH of 1 was then set with ice cooling using conc. sodium hydroxide solution, the precipitate was filtered off with suction and the aqueous phase was extracted three times with 300 ml of ethyl acetate in each case. The water phase was adjusted to pH 12 using conc. sodium hydroxide solution and extracted three times with 400 ml of dichloromethane in each case. The combined dichloromethane phases were dried over sodium sulfate and concentrated. The residue was chromatographed on silica gel using methyl tert-butyl ether/methanol (9:1).

Yield: 21.2 g (37%) of colorless solid.

Melting point: 120° C.

FAB-MS: 190 (M+H)$^+$ 49c. (R or S)-2-Amino-2-(4-cyanophenyl)propionamide 10 g (52.8 mmol) of (R,S)-2-amino-2-(4-cyanophenyl)propionamide were dissolved in 158 ml of methanol, 7.92 g (52.8 mmol) of L-tartaric acid were added, and the mixture was heated until a clear solution was formed and allowed to crystallize overnight at 0° C. The precipitate was filtered off with suction, washed with a little ice-cold methanol and then diethyl ether and recrystallized from methanol.

Yield: 5.2 9 (29%) of colorless solid.

To liberate the (R or S)-2-amino-2-(4-cyanophenyl)propionamide from the tartaric acid salt, the salt was dissolved in water, neutralized with sodium hydrogencarbonate and the free base was extracted three times using 50 ml of methylene chloride in each case.

Yield: 2.75 g (95%) of (R or S)-2-amino-2-(4-cyanophenyl)propionamide, colorless solid,

[α]D=−13.8° (c=0.5; H$_2$O; 22° C.).

FAB-MS: 190 (M+H)$^+$

The enantiomeric purity was determined to be 96% ee on LiChrosorb® Si60 (Merck) after derivatization with R(-)-α-methoxy-α-(trifluoromethyl)phenylacetyl chloride (Mosher reagent).

49d. (R or S)-4-(4-Cyanophenyl)-4-methyl-2,5-dioxoimidazolidine (R or S)-4-(4-Cyanophenyl)-4-methyl-2,5-dioxoimidazolidine was prepared from (R or S)-2-amino-2-(4-cyanophenyl)propionamide using dimethyl carbonate analogously to the procedure indicated in EP-A-173522.

FAB-MS: 216 (M+H)$^+$ 49e. (R or S)-4-(4-Amino-imino-methyl)phenyl)-4-methyl-2,5-dioxoimid-azolidine hydrochloride The preparation of (R or S)-4-(4-(amino-imino-methyl)phenyl)-4-methyl-2,5-dioxoimidazolidine hydrochloride was carried out from (R or S)-4-(4-cyanophenyl)-4-methyl-2,5-dioxoimidazolidine analogously to Example 5.

FAB-MS: 233 (M+H)$^+$

Example 50

(S or R)-4-(4-(Amino-imino-methyl)phenyl)-4-methyl-2,5-dioxo-imidazolidine hydrochloride
(Enantiomer II; the compounds of Examples 49 and 50 are enantiomeric with one another)

50a. (S or R)-2-Amino-2-(4-cyanophenyl)propionamide (S or R)-2-Amino-2-(4-cyanophenyl)propionamide was obtained by resolution of (R,S)-2-amino-2-(4-cyanophenyl)propionamide with D-tartaric acid analogously to Example 49c. Starting from 3.7 g (19.6 mmol) of (R,S)-2-amino-2-(4-cyanophenyl)-propionamide (preparation see Example 49a, b) and after liberation of the base from the salt with D-tartaric acid, 1.05 g (28%) of (S or R)-2-amino-2-(4-cyanophenyl)propionamide were obtained;

[α]D=+13.9° (c=0.5; H$_2$O; 22° C.).

FAB-MS- 190 (M+H)$^+$ 50b. (S or R)-4-(4-(Amino-imino-methyl)phenyl)-4-methyl-2,5-dioxoimid-azolidine hydrochloride The preparation of (S or R)-4-(4-(amino-imino-methyl)phenyl)-4-methyl-2,5-dioxoimidazolidine hydrochloride was carried out from (S or R)-2-amino-2-(4-cyanophenyl)propionamide as mentioned in Example 49d, e.

FAB-MS: 190 (M+H)$^+$

Example 51 (Reaction to give the pharmaceutical active compound)

Ethyl (S)-3-(((S)-4-(4-(amino-imino-methyl)phenyl)-4-methyl-2,5-dioxo-imidazolidin-1-yl)acetylamino)-3-phenylpropionate hydrochloride 440 mg of dicyclohexylcarbodiimide (2 mmol) were added to a solution of 653 mg of (S)-(4-(4-(amino-imino-methyl)phenyl)-4-methyl-2,5-dioxoimid-azolidin-1-yl) acetic acid hydrochloride (2 mmol) (see Example 5), 386 mg of ethyl (S)-3-amino-3-phenylpropionate (2 mmol) and 270 mg of hydroxybenzotriazole in 10 ml of dimethylformamide. The mixture was stirred at 0° C. for one hour and at room temperature for 3 hours and then allowed to stand overnight. The precipitate was filtered off with suction and the filtrate was concentrated. To purify the product, the residue (1.8 g) was chromatographed on Sephadex LH 20 using a mixture of glacial acetic acid, n-butanol and water. The fractions containing the pure substance were concentrated. The residue was dissolved in dilute hydrochloric acid and freeze-dried.

Yield: 597 mg (59.5%)

[α]D=−57° (c=1; H$_2$O; 29° C.).

Example 52 (Reaction to give the pharmaceutical active compound)

Ethyl (S)-3-(((S)-4-(4-(amino-imino-methyl)phenyl)-4-methyl-2,5-dioxo-imidazolidin-1-yl)acetylamino)-3-phenylpropionate hydrochloride 52a. Ethyl (S)-3-(((S)-4-(4-cyanophenyl)-4-methyl-2,5-dioxoimidazolidin-1-yl)acetylamino)-3-phenylpropionate 462 mg of N-ethylmorpholine (4 mmol) were added at 20° C. to a solution of 546 mg of (S)-(4-(4-cyanophenyl)-4-methyl-2,5-dioxoimidazolidin-1-yl)-acetic acid (2 mmol) (see Example 1) and 459 mg of ethyl (S)-3-amino-3-phenylpropionate hydrochloride (2 mmol) in 10 ml of ethyl acetate. The mixture was stirred at 20° C. for 15 min, 656 mg of TOTU (O-((cyano-ethoxycarbonylmethylene)am ino)-N,N, N', N'-tetramethyluronium tetrafluoro-borate) (2 mmol) were then added at this temperature and the mixture was stirred at 20° C. for 2 hours. After addition of 10 ml of water, the mixture was stirred for a further 30 minutes, and after subsequent addition of 10 ml of methyl tert-butyl ether it was stirred at 10° C. for a further 2 hours and the white suspension was filtered off with suction. The product was washed with a mixture of water and ethanol (1:1), then with water, and dried in vacuo.

Yield: 762 mg (85%)
FAB-MS: 449 (M+H)$^+$
M.p. 204–205° C.
[α]D=–67.8° (c=1 CH$_3$OH; 20° C.).

52b. Ethyl (S)-3-(((S)-4-(4-(amino-imino-methyl)phenyl)-4-methyl-2,5-dioxomidazolidin-1-yl)acetylamino)-3-phenylpropionate hydrochloride The cyanophenyl compound of Example 52a was converted into the (amino-imino-methyl)phenyl compound (active compound of Example 51) via the amidoxime according to the procedure in Tetrahedron 42 (1986), 5869.

Example 53 (Reaction to give the pharmaceutical active compound)

Ethyl (S)-3-(((S)-4-(4-(amino-imino-methyl) phenyl)-4-methyl-2,5-dioxo-imidazolidin-1-yl) acetylamino)-3-phenylpropionate acetic acid salt 10.4 ml of N-ethylmorpholine (80 mmol) and 17.6 g of dicyclohexylcarbodiimide (80 mol) were added at 0° C. to a solution of 26.14 g of (S)-(4-(4-(amino-imino-methyl)phenyl)-4-methyl-2,5-dioxoimid-azolidin-1-yl)acetic acid hydrochloride (80 mmol) (see Example 5), 18.37 g of ethyl (S)-3-amino-3-phenylpropionate hydrochloride (80 mmol) and 10.8 g of hydroxybenzotriazole in 400 ml of dimethylformamide. The mixture was stirred at 0° C. for one hour and at room temperature for 3 hours and then allowed to stand overnight. The precipitate was filtered off with suction and the filtrate was concentrated. For purification, the crude product (89 g) was chromatographed on Sephadex LH 20 using a mixture of glacial acetic acid, n-butanol and water. The fractions containing the pure substance were concentrated. The residue was dissolved in water and freeze-dried.

Yield: 35 g (83%) of white powder
[α]D=–55.3° (c=1; H20; 22° C.)
FAB-MS: 466 (M+H)$^+$

We claim:
1. A hydantoin compound of the formula (I) or a salt thereof:

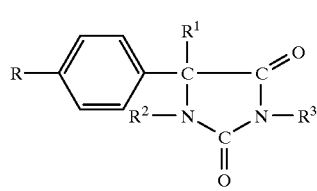

(I)

in which

R is cyano, C(=NH)—O(C$_1$–C$_6$)-alkyl, C(=NH)—NH—X, CH$_2$—NH—X or NH—X$^1$;

X is hydrogen, (C$_1$–C$_6$)-alkyl, (C$_1$–C$_6$)-alkylcarbonyl, (C$_1$–C$_6$)-alkoxycarbonyl, (C$_1$–C$_{18}$)-alkylcarbonyloxy-(C$_1$–C$_6$)-alkoxycarbonyl, unsubstituted or substituted (C$_6$–C$_{14}$)-arylcarbonyl, unsubstituted or substituted (C$_6$–C$_4$)-aryloxycarbonyl, (C$_6$–C$_{14}$)-aryl-(C$_1$–C$_6$)-alkoxycarbonyl unsubstituted or substituted on the aryl radical, (R$^5$O)$_2$P(O), cyano, hydroxyl, (C$_1$–C$_6$)-alkoxy, (C$_6$–C$_{14}$)-aryl-(C$_1$–C$_6$)-alkoxy unsubstituted or substituted on the aryl radical, or amino;

X$^1$ has one of the meanings recited for X or is R'—NH—C(=N—R"), wherein R' and R" independently of one another have one of the meanings recited for X;

R$^1$ is (C$_1$–C$_8$)-alkyl, (C$_6$–C$_{14}$)-aryl-(C$_1$–C$_8$)-alkyl unsubstituted or substitute on the aryl radical, or (C$_3$–C$_8$)-cycloalkyl;

R$^2$ is hydrogen, (C$_1$–C$_8$)-alkyl, unsubstituted or substituted (C$_6$–C$_{14}$)-aryl, (C$_6$–C$_4$)-aryl-(C$_1$–C$_8$)-alkyl unsubstituted or substituted on the aryl radical, or (C$_3$–C$_8$)-cycloalkyl;

R$^3$ is hydrogen or CH$_2$—CO—OR$^4$;

R$^4$ is hydrogen, (C$_1$–C$_6$)-alkyl, (C$_6$–C$_{14}$)-aryl-(C$_1$–C$_6$)-alkyl unsubstituted or substituted on the aryl radical, or unsubstituted or substituted (C$_6$–C$_{14}$)-aryl;

R$^5$ is hydrogen, (C$_1$–C$_8$)-alkyl, unsubstituted or substituted (C$_6$–C$_{14}$)-aryl or (C$_6$–C$_{14}$)-aryl-(C$_1$–C$_8$)-alkyl unsubstituted or substituted on the aryl radical;

with the proylso that, if R$^3$ is hydrogen, R cannot be CN, NH$_2$ or CH$_2$—NH$_2$;

and the proylso that, if the compounds of the formula (I) are present in racemic form with respect to the asymmetric center in the hydantoin ring and at the same time R$^3$ is methoxycarbonylmethyl, R$^1$ is methyl and R$^2$ is hydrogen or methyl, R cannot be CN or C(=NH)—OC$_2$H$_5$;

and the proviso that, if the compounds of the formula (I) are present in racemic form with respect to the asymmetric center in the hydantoin ring and at the same time R$^3$ is methoxycarbonylmethyl or hydroxycarbonylmethyl, R$^1$ is methyl and R$^2$ is hydrogen or methyl, R cannot be NH$_2$, CH$_2$—NH$_2$, C(=NH)—NH$_2$, tert-butoxycarbonyl-aminomethyl or benzyloxycarbonylguanidino;

and the proviso that, if the compounds of the formula (I) are present in racemic form with respect to the asymmetric center in the hydantoin ring and at the same time R$^1$ is methyl and R$^2$ and R$^3$ are hydrogen, R cannot be NH$_2$ or NHCOCH$_3$.

2. A hydantoin compound of the formula (I) or a salt thereof as claimed in claim 1 in which R is cyano or C(=NH)—NH—X;

X is hydrogen, (C$_1$–C$_6$)-alkylcarbonyl, (C$_1$–C$_6$)-alkoxycarbonyl, or unsubstituted or substituted (C$_6$–C$_{14}$)aryl-(C$_1$–C$_6$)-alkoxycarbonyl;

R$^1$ is (C$_1$–C$_8$)-alkyl, (C$_6$–C$_{14}$)-aryl-(C$_1$–C$_8$)-alkyl unsubstituted or substituted on the aryl radical, or (C$_3$–C$_8$)-cycloalkyl;

R$^2$ is hydrogen, (C$_1$–C$_8$)-alkyl, unsubstituted or substituted phenyl, phenyl-(C$_1$–C$_8$)-alkyl unsubstituted or substituted on the phenyl radical, or (C$_3$–C$_8$)-cycloalkyl;

R$^3$ is CH$_2$—CO—OR$^4$;

R$^4$ is hydrogen, (C$_1$–C$_6$)-alkyl, (C$_6$–C$_{14}$)-aryl-(C$_1$–C$_6$)-alkyl unsubstituted or substituted on the aryl radical or unsubstituted or substituted (C$_6$–C$_{14}$)-aryl;

with the proviso that, if the compounds of the formula (I) are present in racemic form with respect to the asymmetric center in the hydantoin ring and at the same time $R^3$ is methyoxycarbonylmethyl, $R^1$ is methyl and $R^2$ is hydrogen or methyl, R cannot be CN;

and the proviso that, if the compounds of the formula (I) are present in racemic form with respect to the asymmetric center in the hydantoin ring and at the same time $R^3$ is methoxycarbonylmethyl or hydroxycarbonylmethyl, $R^1$ is methyl and $R^2$ is hydrogen or methyl, R cannot be $C(=NH)—NH_2$.

3. A hydantoin compound of the formula (I) or a salt thereof as claimed in claim 1, in which R is cyano or $C(=NH)—NH_2$;

$R^1$ is $(C_1–C_4)$-alkyl, cyclopropyl or benzyl;

$R^2$ is hydrogen or $(C_1–C_4)$-alkyl;

$R^3$ is $CH_2—COOH$ or $CH_2—COO—(C_1–C_4)$-alkyl;

with the proviso that, if the compounds of the formula (I) are present in racemic form with respect to the asymmetric center in the hydantoin ring and at the same time $R^3$ is methoxycarbonylmethyl, $R^1$ is methyl and $R^2$ is hydrogen or methyl, R cannot be CN;

and the proviso that, if the compounds of the formula (I) are present in racemic form with respect to the asymmetric center in the hydantoin ring and at the same time $R^3$ is methoxycarbonylmethyl or hydroxycarbonylmethyl, $R^1$ is methyl and $R^2$ is hydrogen or methyl, R cannot be $C(=NH)—NH_2$.

4. A hydantoin compound of the formula (I) or a salt thereof as claimed in claim 3, in which $R^1$ is methyl;

$R^2$ is hydrogen; and $R^3$ is $CH_2—COOH$.

5. A hydantoin compound of the formula (I) or a salt thereof as claimed in claim 1, wherein said hydantoin compound is present in an enantiomerically pure form with respect to the asymmetric center in the hydantoin ring.

6. A hydantoin compound of the formula (I) or a salt thereof as claimed in claim 5, wherein said hydantoin compound is in the S configuration with respect to the asymmetric center in the hydantoin ring.

7. A process for preparing a hydantoin compound of the formula (I) or a salt thereof as claimed in claim 1, which process comprises reacting an amino acid ester of the formula (V):

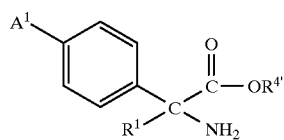
(V)

in which $A^1$ is halogen or nitro, $R^1$ is $(C_1–C_8)$-alkyl, $(C_6–C_{14})$-aryl-$(C_1–C_8)$-alkyl unsubstituted or substituted on the aryl radical or $(C_3–C_8)$-cycloalkyl, and $R^4$ is $(C_1–C_6)$-alkyl, $(C_6–C_{14})$-aryl-$(C_1–C_6)$-alkyl unsubstituted or substituted on the aryl radical, or unsubstituted or substituted $(C_6–C_{14})$-aryl, with an isocyanatoacetic acid ester of the formula (VI):

(VI)

to yield a compound of the formula (VII):

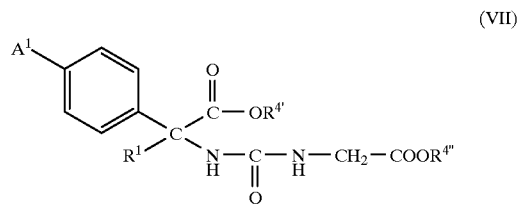
(VII)

cyclizing the compound of formula (VII) obtained from said reaction to give an hydantoin acetic acid of the formula (VIII):

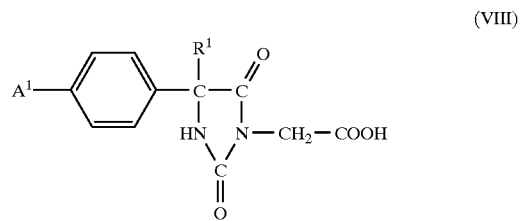
(VIII)

converting the hydantoin acetic acid of formula (VIII) into a compound of the formula (I) by transforming the $A^1$ group of said hydantoin acetic acid of the formula (VIII) into the radical R, the NH group into the $N—R^2$ group and the COOH group into the $COOR^4$ group, or, if a compound of the formula (I) in which $R^3$ is hydrogen is being prepared, converting the amino acid ester of the formula (V) into a hydantoin compound of the formula (III) using a conventional method:

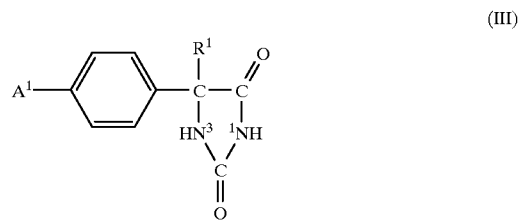
(III)

and subsequently converting the $A^1$ group and the $N^3H$ function of said hydantoin compound of the formula (III) into the radical R and the $N^3—R^2$ group, respectively using a conventional method.

8. A process according to claim 7, in which $A^1$ in formula (V) is bromine.

9. A process according to claim 7, wherein a hydantoin of the formula (I) or a salt thereof is prepared that is enantiomerically pure with respect to the asymmetric center in the hydantoin ring.

10. A process according to claim 9, wherein said enantiomerically pure hydantoin of the formula (I) or a salt thereof has the S configuration with respect to the asymmetric center in the hydantoin ring.

11. A process-for preparing a hydantoin compound of the formula (I) or a salt thereof as claimed in claim 1, which process comprises reacting an amino acid amide of the formula (XI):

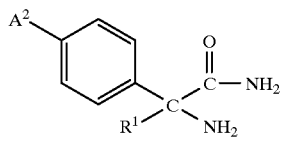

(XI)

in which $A^2$ is halogen, nitro or cyano, and $R^1$ is $(C_1-C_8)$-alkyl, $(C_6-C_{14})$-aryl-$(C_1-C_8)$-alkyl unsubstituted or substituted on the aryl radical, or $(C_3-C_8)$-cycloalkyl, with an isocyanatoacetic acid ester of the formula (VI):

(VI)

to yield a compound of the formula (XII):

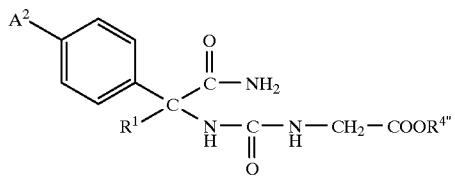

(XII)

cyclizing the compound of formula (XII) obtained from said reaction to give an hydantoin acetic acid of the formula (XIII):

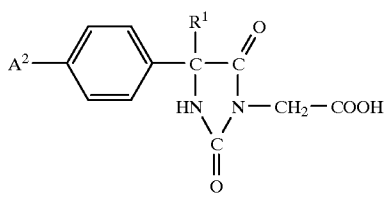

(XIII)

and converting said hydantoin acetic acid of the formula (XIII) into a compound of the formula (I) by transforming the group $A^2$ of said hydantoin acetic acid of the formula (XIII) into the radical R, the NH group into the N—$R^2$ group and the COOH group into the $COOR^4$ group, or, if a compound of the formula (I) in which $R^3$ is hydrogen is being prepared, converting the amino acid amide of the formula (XI) into a hydantoin compound of the formula (XIV) using a conventional method:

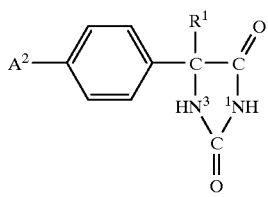

(XIV)

and converting the $A^2$ group and the $N^3H$ function of said hydantoin compound of the formula (XIV) into the radical R and the $N^3$—$R^2$ group, respectively using a conventional method.

12. A process according to claim 11, in which $A^2$ in formula (XI) is bromine.

13. A process according to claim 11, wherein a hydantoin of the formula (I) or a salt thereof is prepared that is enantiomerically pure with respect to the asymmetric center in the hydantoin ring.

14. A process according to claim 13, wherein said enantiomerically pure hydantoin of the formula (I) or a salt thereof has the S configuration with respect to the asymmetric center in the hydantoin ring.

15. A process for preparing a pharmaceutically active compound, which process comprises using a hydantoin compound of the formula (I) or a salt thereof according to claim 1 as an intermediate compound in said process.

16. A process according to claim 15, wherein said pharmaceutically active compound is a compound of the formula (XVI) or a salt thereof:

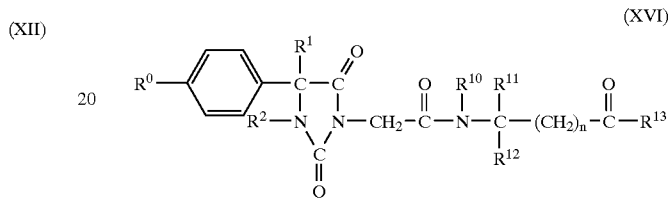

(XVI)

in which $R^0$ is C(=NH)—NH—X, $CH_2$—NH—X or NH—$X^1$;

X is hydrogen, $(C_1-C_6)$-alkyl, $(C_1-C_6)$-alkylcarbonyl, $(C_1-C_6)$-alkoxycarbonyl, $(C_1-C_{18})$-alkylcarbonyloxy-$(C_1-C_6)$-alkoxycarbonyl, unsubstituted or substituted $(C_6-C_{14})$-arylcarbonyl, unsubstituted or substituted $(C_6-C_{14})$-aryloxycarbonyl, $(C_6-C_{14})$-aryl-$(C_1-C_6)$-alkoxycarbonyl unsubstituted or substituted on the aryl radical, $(R^5O)_2P(O)$, cyano, hydroxyl, $(C_1-C_6)$-alkoxy, $(C_6-C_{14})$-aryl-$(C_1-C_6)$-alkoxy unsubstituted or substituted on the aryl radical, or amino;

$X^1$ has one of the meanings recited for X or is R'—NH—C(=N—R''), where R' and R'' independently of one another have one of the meanings recited for X;

$R^1$ is $(C_1-C_8)$-alkyl, $(C_6-C_{14})$-aryl-$(C_1-C_8)$-alkyl unsubstituted or substituted on the aryl radical or $(C_3-C_8)$-cycloalkyl;

$R^2$, $R^{10}$ and $R^{11}$ independently of one another are hydrogen, $(C_1-C_8)$-alkyl, unsubstituted or substituted $(C_6-C_{14})$-aryl, $(C_6-C_{14})$-aryl$(C_1-C_8)$-alkyl unsubstituted or substituted on the aryl radical or $(C_3-C_8)$-cycloalkyl;

$R^5$ is hydrogen, $(C_1-C_8)$-alkyl, unsubstituted or substituted $(C_6-C_{14})$-aryl or $(C_6-C_{14})$-aryl-$(C_1-C_8)$-alkyl, which can be unsubstituted or substituted on the aryl radical;

$R^{12}$ is hydrogen, $(C_1-C_8)$-alkyl, unsubstituted or substituted $(C_6-C_{14})$-aryl, $(C_6-C_{14})$-aryl-$(C_1-C_8)$-alkyl unsubstituted or substituted on the aryl radical, $(C_3-C_8)$-cycloalkyl or 2-, 3- or 4-pyridyl;

$R^{13}$ is hydroxyl, $(C_1-C_{18})$-alkoxy, $(C_6-C_{14})$-aryl-$(C_1-C_8)$-alkoxy unsubstituted or substituted on the aryl radical, unsubstituted or substituted $(C_6-C_{14})$-aryloxy, amino or mono- or di(($C_1-C_{18}$)-alkyl)amino; and n is an integer ranging from 0 to 6.

17. A hydantoin compound of the formula (XVIII) or a salt thereof:

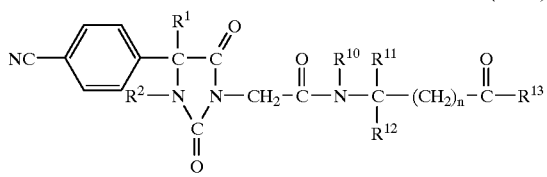

(XVIII)

in which
- $R^1$ is $(C_1-C_8)$-alkyl, $(C_6-C_{14})$-aryl-$(C_1-C_8)$-alkyl unsubstituted or substituted on the aryl radical or $(C_3-C_8)$-cycloalkyl;
- $R^2$, $R^{10}$ and $R^{11}$, independently of one another are hydrogen, $(C_1-C_8)$-alkyl, unsubstituted or substituted $(C_6-C_{14})$-aryl, $(C_6-C_{14})$-aryl-$(C_1-C_8)$-alkyl unsubstituted or substituted on the aryl radical or $(C_3-C_8)$-cycloalkyl;
- $R^{12}$ is hydrogen, $(C_1-C_8)$-alkyl, unsubstituted or substituted $(C_6-C_{14})$-aryl, $(C_6-C_{14})$-aryl-$(C_1-C_8)$-alkyl unsubstituted or substituted on the aryl radical, $(C_3-C_8)$-cycloalkyl or 2-, 3- or 4-pyridyl;
- $R^{13}$ is hydroxyl, $(C_1-C_8)$-alkoxy, $(C_6-C_{14})$-aryl-$(C_1-C_8)$-alkoxy unsubstituted or substituted on the aryl radical, unsubstituted or substituted $(C_6-C_{14})$-aryloxy, amino or mono- or di(($C_1-C_{18}$)-alkyl)amino; and
- n is an integer ranging from 0 to 6.

18. A hydantoin compound of the formula (XVIII) or a salt thereof as claimed in claim 17, in which
- $R^1$ is $(C_1-C_4)$-alkyl, cyclopropyl or benzyl;
- $R^2$ is hydrogen or $(C_1-C_4)$-alkyl;
- $R^{10}$ is hydrogen, $(C_1-C_6)$-alkyl or benzyl;
- $R^{11}$ is hydrogen or $(C_1-C_8)$-alkyl;
- $R^{12}$ is unsubstituted or substituted $(C_6-C_{14})$-aryl or pyridyl;
- $R^{13}$ is hydroxyl or $(C_1-C_8)$-alkoxy; and
- n is an integer ranging from 0 to 3.

19. A hydantoin compound of the formula (XVIII) or a salt thereof as claimed in claim 18, in which
- $R^1$ is methyl;
- $R^2$ is hydrogen;
- $R^{10}$ is hydrogen;
- $R^{11}$ is hydrogen;
- $R^{12}$ is unsubstituted or substituted phenyl;
- $R^{13}$ is hydroxyl or $(C_1-C_4)$-alkoxy;
- n is 1 or 2; and
- a uniform configuration is present at the asymmetric center in the hydantoin ring and at the carbon atom carrying the radicals $R^{11}$ and $R^{12}$.

20. A hydantoin compound of the formula (XVIII) or a salt thereof as claimed in claim 19, in which
- $R^{12}$ is unsubstituted phenyl, n is 1, and
- the S configuration is present at the asymmetric center in the hydantoin ring and at the carbon atom carrying the $R^{11}$ and $R^{12}$ radicals.

21. A process for preparing a hydantoin compound of the formula (XVIII) or a salt thereof as claimed in claim 17, which process comprises reacting a compound of the formula (Ib):

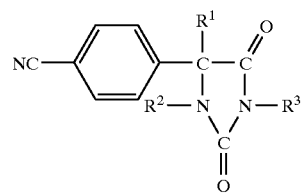

(Ib)

in which $R^1$ and $R^2$ have the meanings given in claim 17 and $R^3$ is $CH_2$—CO—$OR^4$, wherein $R^4$ is hydrogen, $(C_1-C_6)$-alkyl, $(C_6-C_{14})$-aryl-$(C_1-C_6)$-alkyl unsubstituted or substituted on the aryl radical, or unsubstituted or substituted $(C_6-C_{14})$-aryl, with a compound of the formula (XVII):

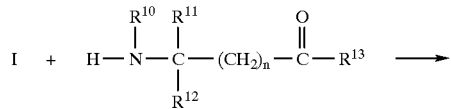

(XVIII)

in which $R^{10}$, $R^{11}$, $R^{12}$, $R^{13}$ and n have the same meaning as recited in claim 17.

22. A process for preparing a pharmaceutically active compound, which process comprises using a compound of the formula (XVIII) or a salt thereof according to claim 17 as an intermediate compound in said process.

* * * * *

UNITED STATES PATENT AND TRADEMARK OFFICE
CERTIFICATE OF CORRECTION

PATENT NO. : 5,939,556
DATED : August 17, 1999
INVENTOR(S) : Zoller, et. al.

It is certified that error appears in the above-identified patent and that said Letters Patent is hereby corrected as shown below:

In Claim 1, col. 26, line 7, "$(C_6-C_4)$-aryloxycarbonyl" should read
--$(C_6-C_{14})$-aryloxycarbonyl--.

In Claim 1, col. 26, line 16, "substitute" should read --substituted--.

In Claim 1, col. 26, line 19, "$(C_6-C_4)$-aryl-$(C_1-C_8)$-alkyl," should
read --$(C_6-C_{14})$-aryl-$(C_1-C_8)$-alkyl--.

In Claim 1, col. 26, line 31, "proylso" should read --proviso--.

In Claim 7, col. 27, line 61, "$R^4$" should read --$R^{4'}$--.

In Claim 11, col. 28, line 64, "process-for" should read --process for--.

In Claim 17, col. 31, line 25, "$(C_1-C_{,8})$-alkoxy" should read
--$(C_1-C_{18})$-alkoxy--.

Signed and Sealed this

Twenty-fourth Day of October, 2000

Attest:

Q. TODD DICKINSON

*Attesting Officer*  *Director of Patents and Trademarks*